United States Patent [19]

Parsons

[11] Patent Number: 4,757,068
[45] Date of Patent: Jul. 12, 1988

[54] LACTAMS AND BICYCLIC LACTAMS USEFUL AS CHOLECYSTOKININ ANTAGONISTS

[75] Inventor: William H. Parsons, Rahway, N.J.

[73] Assignee: Merck & Co., Inc., Rahway, N.J.

[21] Appl. No.: 804,578

[22] Filed: Dec. 4, 1985

Related U.S. Application Data

[62] Division of Ser. No. 624,857, Jun. 26, 1984, abandoned.

[51] Int. Cl.$^4$ .............................................. A61K 31/55
[52] U.S. Cl. .................................... 514/213; 514/212; 514/312; 514/210; 514/183; 514/326; 514/327; 514/408

[58] Field of Search .......................................... 514/213

[56] References Cited

U.S. PATENT DOCUMENTS 4,410,520 10/1983 Watthey .............................. 514/212

Primary Examiner—Frederick E. Waddell
Attorney, Agent, or Firm—Salvatore C. Mitri; R. D. Meredith; Hesna J. Pfeiffer

[57] ABSTRACT

This invention relates to lactams, bicyclic lactams and related compounds which are useful as cholecystokinin antagonists.

2 Claims, No Drawings

LACTAMS AND BICYCLIC LACTAMS USEFUL AS CHOLECYSTOKININ ANTAGONISTS

This is a division of application Ser. No. 624,857, filed June 26, 1984, now abandoned.

BACKGROUND OF INVENTION

Cholecystokinin (CCK) is a neuropeptide composed of thirty-three aminoacids. See: Mutt and Jorpes, *Biochem. J.* 125 678 (1971). The carboxyl terminal octapeptide (CCK-8) also occurs naturally and is fully active. CCK exists in both gastrointestinal tissue and the central nervous system. V. Mutt, *Gastrointestinal Hormones*, G. B. J. Glass, Ed., Raven Press, N.Y., (1980) p. 169. CCK is believed to play an important role in appetite regulation and CCK may be a physiological satiety hormone. G. P. Smith, *Eating and Its Disorders*, A. J. Stunkard and E. Stellar, Eds, Raven Press, New York, 1984, p. 67.

Among additional effects of CCK are stimulation of colonic motility, stimulation of gall bladder contraction, stimulation of pancreatic enzyme secretion, and inhibition of gastric emptying. CCK reportedly co-exists with dopamine in certain mid-brain neurons and thus may also play a role in the functioning of dopaminergic systems in the brain as well as serving as a neurotransmitter in its own right. See: A. J. Prange et al., "Peptides in the Central Nervous System", *Ann. Repts. Med. Chem.* 17 31, 33 (1982) and references cited therein; J. A. Williams, *Biomed. Res.* 3 107 (1982); and J. E. Morley, *Life Sci.* 30, 479 (1982).

CCK antagonists are useful in the treatment and prevention of CCK-related disorders of the gastrointestinal, central nervous and appetite regulatory systems of animals, especially humans. Three distinct chemical classes of CCK receptor antagonists have been reported. One class comprises derivatives of cyclic nucleotides; detailed structure-function studies have demonstrated that of the various members of this class, dibutyryl cyclic GMP is the most potent. See; N. Barlos et al., *Am. J. Physiol.*, 242, G161 (1982) and P. Robberecht et al., *Mol., Pharmacol.*, 17, 268 (1980). The second class comprises peptide antagonists which are C-terminal fragments and analogs of CCK. Recent structure-function studies have shown that both shorter C-terminal fragments of CCK (Boc-Met-Asp-Phe-$NH_2$, Met-Asp-Phe-$NH_2$) as well as longer CCK fragments (Cbz-Tyr(-$SO_3H$)-Met-Gly-Trp-Met-Asp-$NH_2$) can function as CCK antagonists. See: R. T. Jensen et al., *Biochim. Biophys. Acta.*, 757, 250 (1983) and M. Spanarkel et al., *J. Biol. Chem.*, 258, 6746 (1983). The third class of CCK receptor antagonists comprises the amino acid derivatives; proglumide, a derivative of glutaramic acid, and the N-acyl tryptophans including para-chlorobenzoyl-L-tryptophan (benzotript). See W. F. Hahne et al., *Proc. Natl. Acad. Sci. U. S. A.*, 78, 6304 (1981) and R. T. Jensen et al., *Biochem. Biophys. Acta.*, 761, 269 (1983). All of these compounds are relatively weak antagonists of CCK ($IC_{50}$: $10^{-4}-10^{-6}M$).

SUMMARY OF THE INVENTION

It has now been found that compounds of this invention are antagonists of cholecystokinin (CCK). These CCK antagonists are useful in the treatment and prevention of CCK-related disorders of the gastrointestinal, central nervous and appetite regulatory systems of mammals, especially humans.

DETAILED DESCRIPTION OF THE INVENTION

The compounds of this invention are represented by the following formula:

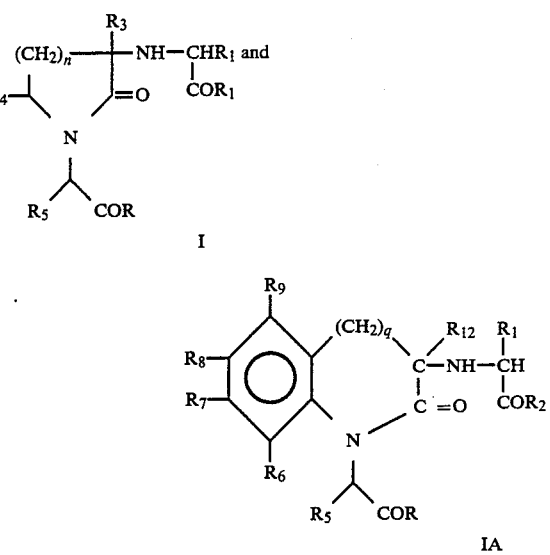

wherein:
R and $R_2$ are independently hydroxyl, loweralkoxy, aryloxy, aralkoxy, and $NR^{10}R^{11}$ wherein $R^{10}$ and $R^{11}$ are independently hydrogen, loweralkyl, loweralkenyl, acyloxyloweralkyl, aryl, aralkyl, carboxyloweralkyl, carboxamidoloweralkyl, substituted loweralkyl wherein the substituents are monohydroxy, dihydroxy, or acylamino;

$R_1$ is
hydrogen;
alkyl of from 1 to 12 carbon atoms which include branched, cyclic and unsaturated alkyl groups;
substituted loweralkyl wherein the substituent can be halo, hydroxy, carboxy, carboxamido, loweralkylthio, loweralkoxy, loweralkoxycarbonyl, loweraralkoxycarbonyl, amino, loweralkylamino, lowerdialkylamino, acylamino; substituted loweralkylamino wherein the substituent can be halo, hydroxy, alkoxy or cyano; arloweralkylamino; cyclic amino; oxo, thio or ureido; aryloxy; arylthio; aralkyloxy; aralkylthio; benzofused cycloalkyl or bicycloalkyl of from 8–12 carbon atoms;
aryl or heteroaryl which may be mono-, di- or trisubstituted by loweralkyl, hydroxy, loweralkoxy, halo, amino, acylamino, loweralkylthio or aminoloweralkyl;
benzofused cycloalkyl or bicycloalkyl of from 8 to 12 carbon atoms;
arloweralkyl; arloweralkenyl; heteroloweralkyl and heteroloweralkenyl in which the aryl or heteroaryl rings may be mono-, di- or tri-substituted by halo, loweralkyl, hydroxy, loweralkoxy, amino, loweralkylamino, diloweralkylamino, aminoloweralkyl, acylamino, carboxy, haloloweralkyl, nitro, cyano or sulfonamido;
aralkyl or heteroaralkyl which include branched loweralkyl groups;

substituted aralkyl or substituted heteroaralkyl which include branched loweralkyl groups wherein the loweralkyl groups can be substituted by amino, acylamino, or hydroxyl and the aryl and heteroaryl groups can be substituted by halo, dihalo, loweralkyl, hydroxy, loweralkoxy, aryloxy, aroyl, arylthio, amino, aminoloweralkyl, loweralkanoylamino, aroylamino, lowerdialkylamino, loweralkylamino, hydroxy, hydroxyloweralkyl, trihaloloweralkyl, nitro, cyano, or sulfonamido;

any of the arloweralkyl or alkenyl and heteroloweralkyl or alkenyl groups described above in which the aryl or heteroaryl ring is partially or completely hydrogenated;

substituted loweralkyl having the formula $R_A{}^1(CH_2)_n-Q-(CH_2)_m$ wherein n is 0-2, m is 1-3, $R_A{}^1$ is aryl or heteroaryl optionally substituted by amino, lowerdialkylamino, loweralkylamino, hydroxy, hydroxyloweralkyl, aminoloweralkyl, trihaloloweralkyl, cyano, nitro, sulfonamido, aroyl, loweralkyl, halo, dihalo, and loweralkoxy, and Q is O, S, SO, $SO_2$, $N-R_B{}^1$, $CONR_C{}^1$, $NR_C{}^1CO$, $CH=CH$ wherein $R_B{}^1$ is hydrogen, loweralkyl, aryl, aralkyl, loweralkanoyl, or aroyl, and $R_C{}^1$ is hydrogen, or loweralkyl;

$R_3$ is hydrogen, loweralkyl;

$R_4$ is hydrogen, loweralkyl, aryl, substituted aryl wherein the substituent is halo, alkyl, or alkoxy;

$R_5$ is hydrogen, loweralkyl, aryl;

$R_6$ $R_7$, $R_8$ and $R_9$ can be the same or different or each can independently be hydrogen, loweralkyl, loweralkoxy, halo;

$R_{12}$ is loweralkyl;

n is 1-4;

q is 0-3; and, the pharmaceutically acceptable salts thereof.

The alkyl substituents recited above denote straight and branched chain hydrocarbons of $C_1-C_{12}$ such as methyl, hexyl, propyl, dodecyl isopentyl isopropyl, nopentyl, etc.

Loweralkyl denotes alkyl groups of $C_1$ to $C_8$ such as ethyl, isobutyl, 4-methylpentyl, and the like.

Alkenyl and alkynyl denote alkyl groups as described above which are modified so that each contains a carbon to carbon double bond or triple bond, respectively, such as vinyl, 2-butenyl and 1-hexynyl.

Cycloalkyl denotes rings composed of 5 to 8 methylene groups, each which may be substituted or unsubstituted with other hydrocarbon substituents, and include, for example, cyclopentyl, cycloheptyl, 4-methyl cyclohexyl, and the like.

Benzofused cycloalkyl groups denote a cycloalkyl ring of 5 to 8 carbon atoms to which is fused a benzene ring such as indanyl or tetralyl groups.

Bicycloalkyl denotes two cycloalkyl rings of 5 to 8 carbon atoms each joined together in any allowable way such as perhydroindane, octahydronaphthalene, bicyclo 3:1:3 octane and spiro 4:0:4 nonane.

The loweralkoxy substituent represents a loweralkyl group as described above attached through an oxygen bridge.

The aralkyl and heteroaralkyl substituents recited above represent aryl or heteroaryl groups as herein defined attached through a straight or branched chain hydrocarbon of from one to six carbon atoms, for example, benzyl, phenethyl, 3,3-diphenylpropyl, 3-indolylmethyl, and the like.

Halo means chloro, bromo, iodo, or fluoro.

The aryl substituent represents phenyl, naphthyl, or biphenyl.

The heteroaryl substituent recited above represents any 5- or 6-membered aromatic ring containing from one to three heteroatoms selected from the group consisting of nitrogen, oxygen, and sulfur, for example, pyridyl, thienyl, furyl, imidazolyl, and thiazolyl; as well as any bicyclic group in which any of the above heterocyclic rings is fused to another aromatic ring, for example, indolyl, quinolinyl, isoquinolinyl, benzimidazolyl, benzothiazolyl, benzthienyl, and naphthyridyl.

The acylamino substituent represents loweralkanoylamino and aroylamino.

The compounds of Formula I and IA can be produced by the methods shown in the following Reaction Schemes wherein $R_1-R_9$, $R_{12}$, n, and q are as defined above unless otherwise indicated.

Reaction Scheme A

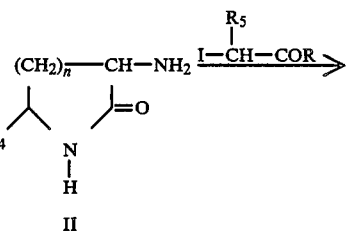

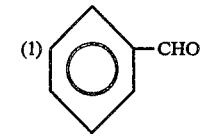

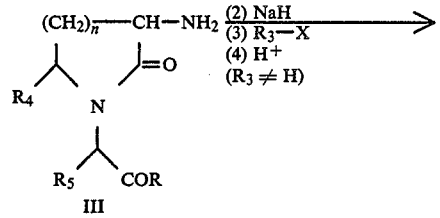

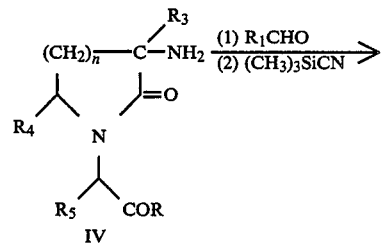

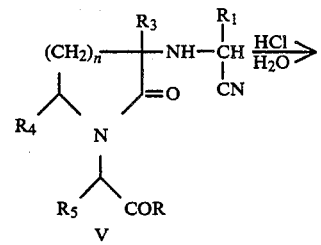

-continued
Reaction Scheme A

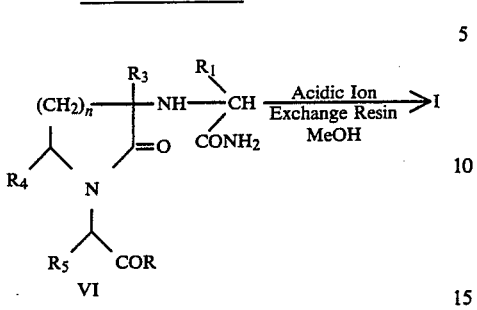

Reaction Scheme B

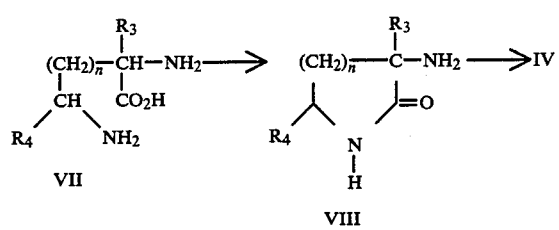

Reaction Scheme C

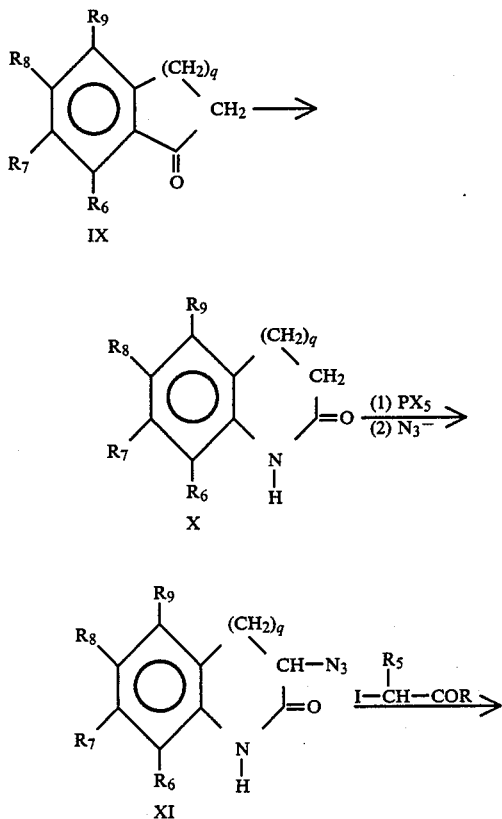

-continued
Reaction Scheme C

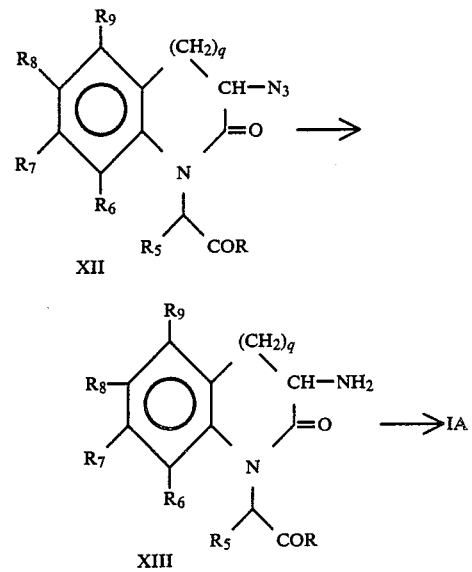

Reaction Scheme D (n = 0)

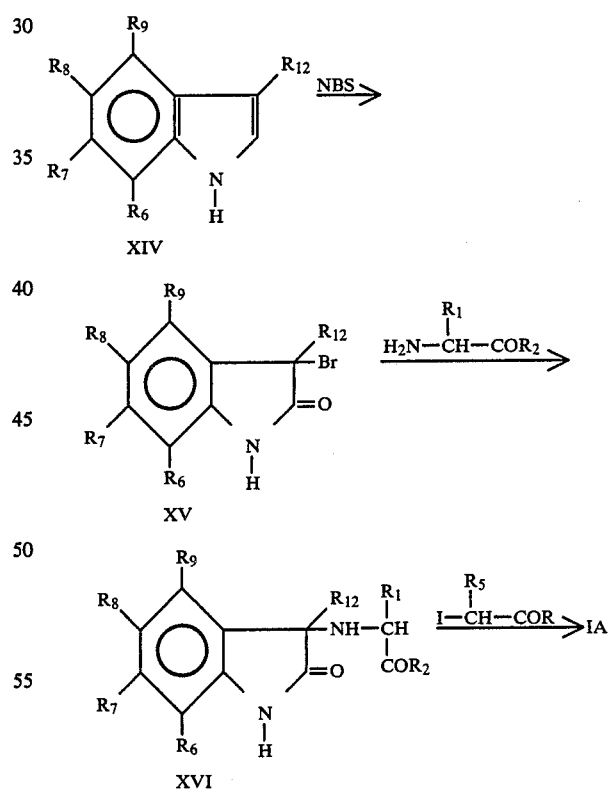

As shown in Reaction Scheme A, 3-aminolactam II (n=1–3) is alkylated on the amido nitrogen with an iodoester in the Presence of a strong base such as sodium hydride or Potassium t-butoxide in a suitable solvent such as tetrahydrofuran or dimethylformamide. Reaction of the alkylated lactam III with benzaldehyde in a solvent such as methylene chloride in the Presence of a dessicant such as, for example, sodium sulfate. Produces an aldimine. Treatment of this aldimine with a base in a suitable solvent, for example sodium hydride, in dimethylformamide, produces an anion which can be reacted with an alkylating agent such as methyl iodide. Hydrolysis of the resulting alkylat ed aldimine in aqueous acid produces IV.

Alternatively, IV can be prepared by cyclizing the desired diamino acid VII (Reaction Scheme B). For example. Preparation of the diaminoacid ester hydrochloride from VII and an alcohol such as ethanol in the Presence of hydrogen chloride followed by neutralization and refluxing in a solvent such as ethanol Produces VIII. Alkylation of VIII as described for II above affords IV.

Reaction of IV with an aldehyde produces an aldimine which can be reacted with trimethylsilyl cyanide (Reaction Scheme A) in the Presence of a zinc salt such as the iodide in an inert solvent, for example methylene chloride, to afford, after aqueous workup, V. Treatment of V with concentrated hydrochloric acid converts the nitrile to the amide VI wherein R=OH which, upon treatment with an acidic ion exchange resin in an alcohol such as, for example methanol, produces I as the corresponding diester (e.g., $R_2=R=OCH_3$). If desired, the diesters I can be hydrolyzed by dilute base to afford the diacids I ($R_2=R=OH$).

In Reaction Scheme C, benzofused structures IA (q=1,2) are synthesized from ketones IX. Beckmann or Schmidt (L. Donamura, W. Z. Heldt, *Organic Reactions*, 1960, 11, 1–156) rearrangement of IX under standard conditions affords lactams X. Halogenation of X using phosphorus pentahalides in a suitable solvent such as chloroform followed by displacement of the halide with azide (e.g. sodium or lithium azide) in a solvent such as dimethylformamide affords azido lactam XI. Alkylation of XI as described above for II (Reaction Scheme A) affords XII. Reduction of the azide using, for example, hydrogen and palladium on charcoal, produces amine XIII. Reaction of this amine as described above for IV (Reaction Scheme A) yields IA (q=1,2).

For lactams IA where q=0 (Reaction Scheme D), bromination of indoles XIV with N-bromosuccinimide in t-butanol (R. L. Hinman, C. P. Bauman, *J. Org. Chem.* 1964, 29, 1206) affords bromooxindoles XV. Reaction of XV with an amino ester in a solvent such as ether affords XVI which can be alkylated with an iodoester as described for II (Reaction Scheme A) to afford diesters IA. If desired, the diacids ($R_2=R=OH$) can be obtained by hydrolysis such as, for example, of the diesters.

Preferred diastereomers of the invention compounds are isolated by chromatography or crystallization of intermediates or the end products or their salts. One can also resolve intermediates by the use of optically active salts or bases. Finally, if desired, compounds of this invention can also be employed as a mixture of their enantiomers or diastereomers.

The α-keto acids and α-keto esters IX utilized in the process of the invention are known in the art or can be made by numerous, known methods. For example, synthons such as

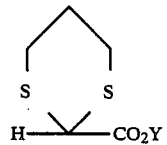

can be converted to α-keto acids or esters using methods involving alkylation followed by hydrolysis as described in the literature. An excellent method involves the reaction of Grignard reagents $R_1MgX$ with $ClCOCO_2Y$ or $YO_2CCO_2Y$. Another method involves condensing substituted acetic acid esters with diethyl oxalate followed by hydrolytic decarboxylation under acidic conditions to obtain α-keto acids. Carefully controlled acid hydrolysis in alcohol of acyl cyanides, which are prepared from acid chlorides and cuprous cyanide, also proves to be a viable synthetic route to α-keto esters. Nucleophilic displacement reactions on chloro or bromo pyvuric acid (ester) can also be used to produce a variety of interesting α-keto acids (esters). In these formulae, Y is a group such as loweralkyl or benzyl and protecting groups are employed as necessary in the $R_1$ group if interfering functionality is present.

The compounds of this invention form salts with various inorganic and organic acids and bases which are also within the scope of the invention. Such salts include ammonium salts, alkali metal salts like sodium and potassium salts, alkaline earth metal salts like the calcium and magnesium salts, salts with organic bases e.g., dicyclohexylamine salts, N-methyl-D-glucamine, salts with amino acids like arginine, lysine and the like. Also salts with organic and inorganic acids may be prepared, e.g., HCl, HBr, $H_2SO_4$, $H_3PO_4$, methanesulfonic, toluenesulfonic, maleic, fumaric, camphorsulfonic. The non-toxic physiologically acceptable salts are preferred, although other salts are also useful, e.g., in isolating or purifying the product.

The salts may be formed by conventional means as by reacting the free acid or free base forms of the product with one or more equivalents of the appropriate base or acid in a solvent or medium in which the salt is insoluble, or in a solvent such as water which is then removed in vacuo or by freeze-drying or by exchanging the cations of an existing salt for another cation on a suitable ion exchange resin.

An embodiment of this invention is the preparation of compounds of Formula I and IA.

Another embodiment is the use of the compounds of Formula I and IA for the treatment and the prevention of CCK-related disorders of the gastrointestinal, central nervous, and appetite regulatory systems of mammals, especially of man. Specifically, the Formula I and IA compounds are useful in treatment and prevention of disorders of gastric acid secretion, gastrointestinal motility, pancreatic secretions, and dopaminergic functions. The compounds of Formula I and IA are especially useful in the prevention and treatment of irritable bowel syndrome.

A further embodiment is a composition comprising an effective amount of a compound of Formula I and IA and a pharmaceutically acceptable carrier.

The ability of the compounds of Formula I and IA to antagonize CCK makes these compounds useful as pharmaceutical agents. These compounds will be especially useful in the treatment and prevention of disease states wherein CCK may be involved, for example, gastrointestinal disorders such as irritable bowel syndrome, ulcers, excess pancreatic or gastric secretion, acute pancreatitis, motility disorders, central nervous system disorders caused by CCK's interaction with dopamine such as neuroleptic disorders, tardive dyskinesia, Parkinson's disease, psychosis or Gilles de la Tourette Syndrome, and disorders of appetite regulatory systems.

The compounds of Formula I and IA or pharmaceutically acceptable salts thereof, can be administered to a human subject either alone, or preferably, in combination with pharmaceutically acceptable carriers or diluents, in a pharmaceutical composition, according to standard pharmaceutical practice.

Conventional procedures for preparing such compositions in appropriate dosage forms can be utilized. Whatever the dosage form, it will contain a pharmaceutically effective amount of the present composition.

The present compositions can be administered orally or other than orally; e.g., parenterally, by insufflation, topically, rectally, etc.; using appropriate dosage forms; e.g., tablets, capsules, suspensions, solutions, and the like, for oral administration; suspension emulsions, and the like, for parenteral administration; solutions for intravenous administration; and ointments, transdermal patches, and the like, for topical administration.

Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparation. Tablets containing the active ingredient in admixture with non-toxic pharmaceutically acceptable excipients may also be manufactured by known methods. The excipients used may be for example, (1) inert diluents such as calcium carbonate, sodium carbonate, lactose, calcium phosphate or sodium phosphate; (2) granulating and disintegrating agents such as corn starch, or alginic acid; (3) binding agents such as starch, gelatin or acacia, and (4) lubricating agents such as magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in U.S. Pat. Nos. 4,256,108; 4,160,452; and 4,265,874 to form osmotic therapeutic tablets for controlled release.

In some cases, formulations for oral use may be in the form of hard gelatin capsules wherein the active ingredient is mixed with an inert solid diluent, for example, calcium carbonate, calcium phosphate or kaolin. They may also be in the form of soft gelatin capsules wherein the active ingredient is mixed with water or an oil medium, for example peanut oil, liquid paraffin, or olive oil.

Aqueous suspensions normally contain the active materials in admixture with excipients suitable for the manufacture of aqueous suspensions. Such excipients may be (1) suspending agents such as sodium carboxymethylcellulose, methylcellulose, hydroxypropylmethylcellulose, sodium alginate, polyvinylpyrrolidone, gum tragacanth and gum acacia;

(2) dispersing or wetting agents which may be (a) a naturally-occurring phosphatide such as lecithin, (b) a condensation product of an alkylene oxide with a fatty acid, for example, polyoxyethylene stearate, (c) a condensation product of ethylene oxide with a long chain aliphatic alcohol, for example, heptadecaethyleneoxycetanol, (d) a condensation product of ethylene oxide with a partial ester derived from a fatty acid and a hexitol such as polyoxyethylene sorbitol monooleate, or (e) a condensation product of ethylene oxide with a partial ester derived from a fatty acid and a hexitol anhydride, for example polyoxyethylene sorbitan monooleate.

The aqueous suspensions may also contain one or more preservatives, for example, ethyl or n-propyl p-hydroxybenzoate; one or more coloring agents; one or more flavoring agents; and one or more sweetening agents such as sucrose or saccharin.

Oily suspension may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents and flavoring agents may be added to provide a palatable oral preparation. These compositions may be preserved by the addition of an antioxidant such as ascorbic acid.

Dispersible powders and granules are suitable for the preparation of an aqueous suspension. They provide the active ingredient in admixture with a dispersing or wetting agent, a suspending agent and one or more preservatives. Suitable dispersing or wetting agents and suspending agents are exemplified by those already mentioned above. Additional excipients, for example, those sweetening, flavoring and coloring agents described above may also be present.

The pharmaceutical compositions of the invention may also be in the form of oil-in-water emulsions. The oily phase may be a vegetable oil such as olive oil or arachis oils, or a mineral oil such as liquid paraffin or a mixture thereof. Suitable emulsifying agents may be (1) naturally-occurring gums such as gum acacia and gum tragacanth, (2) naturally-occurring phosphatides such as soy bean and lecithin, (3)esters or partial esters derived from fatty acids and hexitol anhydrides, for example, sorbitan monooleate, (4) condensation products of said partial esters with ethylene oxide, for example, polyoxyethylene sorbitan monooleate. The emulsions may also contain sweetening and flavoring agents.

Syrups and elixirs may be formulated with sweetening agents, for example, glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to known methods using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

A composition of the invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compositions of the invention are employed.

Treatment dosage for human beings can be varied as necessary. Generally, daily dosages of the composition of the invention for use as a CCK antagonist can range from about 0.5 mg to about 1000 mg; preferably, from about 5 mg to about 500 mg.

The amount of active ingredient that may be combined with the carrier materials to produce a single dosage form will vary depending upon the host treated and the particular mode of administration. For example, a formulation intended for oral administration may contain from 5 mg to 500 mg of active agents compounded with an appropriate and convenient amount of carrier material which may vary from about 5 to about 95 percent of the total composition.

It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

The compounds of this invention can also be administered in combination with other pharmaceutical agents such as antihypertensives and/or diuretics and/or calcium entry blockers.

IN VITRO ACTIVITY OF FORMULA I

The biological activity of the compounds of Formula I and IA have been evaluated using an $^{125}$I-CCK receptor binding assay and in vitro isolated tissue preparations.

MATERIALS AND METHODS

1. CCK Receptor Binding (Pancreas)

CCK-33 was radiolabeled with $^{125}$I-Bolton Hunter reagent (2000 Ci/mmole) as described by Sankara et al. (*J. Biol. Chem.* 254: 9349–9351, 1979). Receptor binding was performed according to Innis and Snyder (*Proc. Natl. Acad. Sci.* 77: 6917–6921, 1980) with the minor modification of adding the additional protease inhibitors, phenylmethane sulfonyl fluoride and o-phenanthroline. The latter two compounds have no effect on the $^{125}$I-CCK receptor binding assay.

Male Sprague-Dawley rats (200–350g) were sacrificed by decapitation. The whole pancreas was dissected free of fat tissue and was homogenized in 20 volumes of ice-cold 50 mM, Tris HCl (pH 7.7 at 25° C.) with a Brinkmann Polytron PT 10. The homogenates were centrifuged at 48,000 g for 10 min. Pellets were resuspended in Tris Buffer, centrifuged as above and resuspended in 200 volumes of binding assay buffer (50 mM Tris HCl, pH 7.7 at 25° C., 5 mM dithriothriethel, 0.1 mM bacitracin, 1.2 mM phenylmethane sulfonyl fluoride, and 0.5 mM phenathroline). For the binding assay, 25 μl of buffer (for total binding) or unlabeled CCK-8 sulfate to give a final concentration of 1 μM (for nonspecific binding) or the compounds of Formula I and IA (for determination inhibition of $^{125}$I-CCK binding) and 25 μl of $^{125}$I-CCK-33 (30,000–40,000 cpm) were added to 450 μl of the membrane suspensions in microfuge tubes. All assays were run in duplicate or triplicate. The reaction mixtures were incubated at 37° C. for 30 minutes and centrifuged in a Beckman Microfuge (4 minutes) immediately after adding 1 ml of ice-cold incubation buffer. The supernatant was aspirated and discarded, pellets were counted with a Beckman gamma 5000.

2. CCK Receptor Binding (Brain)

CCK-33 was radiolabeled and the binding was performed according to the description for the pancreas method with modifications according to Saito et al. (*J. Neurochem.*, 37, 483–490 (1981)).

Male Hartley guinea pigs (300–500g) were sacrificed by decapitation and the brains were removed and placed in ice-cold 50 mM, Tris HCl plus 7.58 g/l Tritma-7.4 (pH 7.4 at 25° C.) Cerebral cortex was dissected and used as a receptor source. Each gram of fresh guinea pig brain tissue was homogenized in 10 ml of Tris/Trizma buffer with a Brinkman polytron PT-10. The homogenates were centrifuged at 42,000 g for 15 min. Pellets were resuspended in Tris Buffer, centrifuged as above and resuspended in 200 volumes of binding assay buffer (10 mM HEPES, pH 7.7 at 25° C., 5 mM MgCl$_2$, 1 mM EGTA, 0.4% BSA (bovine serum albumin), and 0.25 mg/ml bacitracin). For the binding assay, 25 μl of buffer (for total binding) or unlabeled CCK-8 sulfate to give a final concentration of 1 μM (for nonspecific binding) or the compounds of Formula I and IA (for determination inhibition of $^{125}$I-CCK binding) and 25 μl of $^{125}$I-CCK-33 (30,000–40,000 cpm) were added to 450 μl of the membrane suspensions in microfuge tubes. All assays were run in duplicate or triplicate. The reaction mixtures were incubated at 25° C. for 2 hours and centrifuged in a Beckman Microfuge (4 minutes) immediately after adding 1 ml of ice-cold incubation buffer. The supernatant was aspirated and discarded, pellets were counted with a Beckman gamma 5000.

IN VITRO RESULTS

1. Effect of the Compounds of Formula I and IA on $^{125}$I-CCK-33 Receptor Binding Compounds of Formula I and IA inhibited specific $^{125}$I-CCK-33 binding in a concentration dependent manner with an IC$_{50}$ less than or equal to 100 μM such as, for example:

1-carbomethoxymethyl-3-(1-carbethoxy-3-phenyl-propyl)-amino-7-phenylperhydroazepin-2-one, IC$_{50}$=32 μM; and, 1-carbomethoxymethyl-3-(1-carbomethoxy-3-phenyl-propyl)-amino-3-methyl homodihydrocarbostyril, IC$_{50}$=72 μM.

The following examples are illustrative of the invention and constitute especially preferred embodiments. The preferred diastereomers of these examples are isolated by conventional column chromatography or fractional crystallization. Unless otherwise indicated, all temperatures are in degrees Celsius.

EXAMPLE 1

1-Carboxymethyl-3-(1-carboxy-3-phenylpropyl)amino-3-methyl-2-pyrrolidone

Step A: 3-Amino-3-methyl-2-pyrrolidone

Excess diazomethane in ether was reacted with 2-methylacrylic acid in ether to afford 3H-4,5-dihydro-3-methoxycarbonyl-3-methylpyrazole (K. V. Auwers and F. Konig, *Ann.* 1932, 496, 27–51) which is reduced over Raney nickel (H. E. Carter et al., *J. Biol. Chem.* 1949, 178, 325–334). After filtering, the reaction was kept at room temperature for several hours then concentrated to afford the desired lactam, m.p. 86–88.

Step B: 1-t-Butoxycarbonylmethyl-3-amino-3-methyl-2-pyrrolidone

To a suspension of 250 mg sodium hydride in 25 ml tetrahydrofuran was added 1.14 g of the Step A aminolactam portionwise as a solid. After 10 minutes, a solution of 2.45 g t-butyl iodoacetate in 8 ml tetrahydrofuran was added dropwise. After stirring for 2 hours, the reaction was quenched with ice water. Ether and brine were then added, the aqueous layer separated and extracted with ether, and the organic phases combined and dried. Concentration afforded the desired compound as a crystalline solid, m.p. 72°–77°.

Step C: 1-t-Butoxycarbonylmethyl-3-(1-cyano-3-phenylpropyl)amino-3-methyl-2-pyrrolidone A mixture of 1.72 g of aminolactam (Step B), 1.01 g 3-phenylpropionaldehyde and anhydrous sodium sulfate in 30 ml dichloromethane was stirred at ambient temperature for 2 hours. The reaction was filtered and 0.80 g trimethylsilyl cyanide and a few mg zinc iodide were added to the filtrate. The reaction was stirred at room temperature for 22 hours then quenched with water. The organic phase was separated, dried and concentrated to afford the desired diastereomeric nitriles.

Step D: 1-Methoxycarbonylmethyl-3-(1-carboxamido-3-phenylpropyl)amino-3-methyl-2-pyrrolidone A solution of 2.0 g of the nitrile (Step C) in 30 ml 12N hydrochloric acid was kept at room temperature for 4 days. The reaction was then filtered and concentrated after which the residue was dissolved in 25 ml saturated methanolic hydrogen chloride. After 24 hours, the reaction was concentrated and the partially solid residue was partitioned between ethyl acetate and aqueous potassium carbonate. After drying and concentration of the organic phase, the crude desired product was isolated as an oil.

Chromatography over silica gel (9 ethylacetate:1 acetonitrile) provided the pure diastereomers of the desired product (Isomer A—first to elute, Isomer B—second to elute).

Step E: 1-Methoxycarbonylmethyl-3-(1-methoxycarbonyl-3-phenylpropyl)amino-3-methyl-2-pyrrolidone Each of the diastereomers from Step D was converted to the desired diester by heating in methanol with an acidic ion exchange resin (W. Greenlee and E. D. Thorsett, *J. Org. Chem.* 1981, 46, 5351–5353).

Isomer A: NMR (CDCl₃): δ1.25 (s, 3H); 1.6–2.2 (m, 4H); 2.5–2.9 (m, 3H); 3.2–3.7 (m, 3H); 3.67 (s, 3H); 3.70 (s, 3H); 4.0 (2xd, 2H, J=18); 7.15 (s, 5H).

Isomer B: NMR (CDCl₃) 1.25 (s, 3H); 1.6–2.1 (m, 4H) 2.4–3.0 (m bs, 3H); 3.2–3.65 (m, 3H); 3.67 (s, 6H); 4.0 (2xd, 2H, J=16); 7.2 (s, 5H).

Step F: 1-Carboxymethyl-3-(1-carboxy-3-phenylpropyl) amino-3-methyl-2-pyrrolidone Each of the diasteromeric diesters from Step E was hydrolyzed in dilute methanolic sodium hydroxide. Purification was by chromatography over an acidic ion exchange resin eluting with aqueous pyridine. After freeze drying, the isomeric diacids were isolated as white powders.

Diacid from isomer A, step D: Anal. (C₁₇H₂₂N₂O₅.¼H₂O): Calc.: C, 59.99; H, 6.66; N, 8.23. Found: C, 59.92; H, 6.61; N, 8.49.

Diacid from isomer B, step D: Anal. (C₁₇H₂₂N₂O₅.½H₂O): Calc.: C, 59.45; H, 6.69; N, 8.15. Found: C, 59.36; H, 6.57; N, 8.36.

EXAMPLE 2

1-Carboxymethyl-3-(1-carboxy-3-phenylpropyl)amino-3-methyl-2-piperidone

3-Amino-3-methyl-2-piperidone (P. Bey, et al., *J. Med. Chem.* 1978, 21, 50–55) was converted to 1-methoxycarbonylmethyl-3-(1-carboxamido-3-phenylpropyl)amino-3-methyl-2-piperidone following Example 1, Steps B-D, at which point the diastereomers were separated. Following Steps E and F of Example 1, these amides were converted to the desired isomeric diacids.

Diacid from isomer A, step D: NMR (D₂O): δ1.65 (s); 1.9–2.4 (m); 2.6–3.0 (m); 3.3–3.8 (m); 4.1 (2×d); 7.3 (s).

Diacid from isomer B, step D: NMR (D₂O): δ1.75 (s); 1.9–2.6 (m); 2.7–3.1 (m); 3.3–3.5 (m); 3.9 (t); 4.15 (2×d); 7.4 (s).

EXAMPLE 3

1-Carboxymethyl-3-(1-carboxy-3-phenylpropyl)amino-3-methylperhydro-2-azepinone

3-Aminoperhydro-2-azepinone (R. Pellegata, et al., *Synthesis,* 1978, 614–616) was alkylated with t-butyl iodoacetate as described in Example 1, Step B, to afford 1-t-butoxycarbonylmethyl-3-aminoperhydro-2-azepinone.

This amino ester (12.13 g) was dissolved in 150 ml dichloromethane and treated with 5.31 g benzaldehyde and excess anhydrous magnesium sulfate. After stirring at room temperature overnight, the reaction was filtered and concentrated to a solid. Recrystallization from ethanol-water afforded pure 1-t-butoxycarbonylmethyl-3-benzaliminoperhydro-2-azepinone, m.p. 131–133.

A solution of the above benzalimine (6.60 g) in 100 ml dimethylformamide was stirred with 0.50 g sodium hydride at 41° for 4 hours. The reaction was cooled to room temperature while 2.85 g methyl iodide was added at such a rate as to maintain the temperature at less than 30°. After stirring for 30 minutes at room temperature, the reaction was concentrated and the residue partitioned between water and ethyl acetate. Concentration of the organic phase afforded the crude alkylation product which was hydrolyzed in 150 ml 5% sodium dihydrogen phosphate solution containing 30 ml acetonitrile. Phosphoric acid was added during the course of the reaction to maintain pH 4-4.5. After 2 hours, the reaction was extracted with ether to remove benzaldehyde, then the aqueous phase was raised to pH 11 with potassium carbonate and extracted with ethyl acetate. Concentration of the extracts afforded 1-t-butoxycarbonylmethyl-3-amino-3-methylperhydro-2-azepinone.

Following the procedure of Example 1, Step C, the above amine was converted to 1-t-butyoxy-carbonylmethyl-3-(1-cyano-3-phenylpropyl)amino-3-methylperhydro-2-azepinone at which point the diasteromers were separated.

TLC (silica, 7 hexane:3 ethyl acetate): $R_f$=0.42 (isomer A); 0.53 (isomer B).

Following the procedure of Example 1, Steps D-F, each of the above diastereomeric nitriles was converted to the desired diacid.

Diacid from isomer A (above): TLC (silica, 3-ethylacetate: 1 acetic acid:1 water: 1 butanol) $R_f$=0.46.

Anal. ($C_{19}H_{26}N_2O_5 \cdot \frac{3}{4}H_2O$). Calc.: C, 60.70; H, 7.31; N, 7.44. Found: C, 60.94; H, 7.11; N, 7.45.

Diacid from isomer B (above): TLC (as for isomer A) $R_f$=0.50.

Anal. ($C_{19}H_{26}N_2O_5 \cdot 3/5\ H_2O$). Calc.: C, 61.14; H, 7.28; N, 7.50 Found: C, 61.26; H, 7.40; N, 7.46.

EXAMPLE 4

1-Carboxymethyl-3-(1-carboxy-3-phenylpropyl)amino-3-methyl-1,2-dihydro-2-oxo-3H-indole A solution of 2.5 g 3-bromo-3-methyloxindole, 2 g ethyl 2-amino-4-phenylbutyrate and 1.6 ml triethylamine in 150 ml ether was refluxed for 48 hours. The resulting crude product was partitioned between 50% potassium carbonate solution and ethyl acetate. The organic phase was dried (MgSO$_4$) and concentrated. Chromatography at the residue (silica, ether) afforded 3-(1-ethoxycarbonyl-3-phenylpropyl)amino-3-methyl-1,2-dihydro-2-oxo-3H-indole as a mixture of diastereomers.

This above lactam was alkylated with t-butyliodoacetate as described in Example 1, Step B, to afford, after chromatography (silica, 2 ether: 1 hexane), 1-t-butyoxycarbonylmethyl 3-(1-ethoxy-carbonyl-3-phenylpropyl)amino-3-methyl-1,2-dihydro-2-oxo-3H-indole. NMR (CDCl$_3$): δ1.1 (t, 3H); 1.5 (s, 9H); 1.55 (s, 3H); 1.8-3.2 (m, 6H); 3.9 (s, 2H); 4.4 (s, 2H); 7.1 (br.s., 9).

Treatment of the diester with trifluoroacetic acid followed by alkaline hydrolysis and chromatography over an acidic ion exchange resin afforded the title diacids.

NMR (D$_2$O, H$_2$O=4.6): δ1.4 (s, 3H); 1.5-1.8 (m, 2H); 1.2-1.7 (m, 3H); 4.1,4.2 (2s, 2H); 6.8-7.2 (br.s., 9H).

Anal. ($C_{21}H_{22}N_2O_5 \cdot \frac{1}{4}H_2O$). Calc.: C, 65.11; H, 5.68; N, 7.23. Found: C, 65.14; H, 5.76; N, 7.47.

TLC (silica, 1 n-butanol: 1 ethylacetate: 1 water: 5 acetic acid). $R_f$=0.61.

EXAMPLE 5

1-Carboxymethyl-3-(1-carboxy-3-phenylpropyl)amino-3-methyl-2-oxo-1,2,3,4-tetrahydroquinoline 3-Amino-3-methyl-2-oxo-1,2,3,4-tetrahydroquinoline (T. J. McCord, et al., *J. Heterocyclic Chem.*, 980, 17 1405) was converted to the diastereomeric title compounds as described in Example 1, Steps B-F.

Isomer A. NMR (D$_2$O, H$_2$O=4.6): 1.0 (s, 3H); 1.6-3.0 (m, 6H); 3.7 (t, 1H); 4.2 (q, 2H); 6.8 (br.s, 9H).

Anal. ($C_{22}H_{23}N_2O_5Na$). Calc.: C, 64.95; H, 5.78; N, 6.88. Found: C, 65.38; H, 6.07; N, 6.79.

Isomer B. NMR (D$_2$O, H$_2$O=4.6): δ1.1 (s, 3H), 1.6-3.0 (m, 6H); 4.2 (q, 2H); 6.9 (br.s, 9H).

Anal. ($C_{22}H_{23}N_2O_5Na$). Calc.: C, 64.95; H, 5.78; N, 6.88. Found: C, 64.80; H, 6.16; N, 6.57.

EXAMPLE 6

1-Carboxymethyl-3-(1-carboxy-3-phenylpropyl)amino-3-methyl-2,3,4,5-tetrahydro-1H-1-benzazepin-2-one To a solution of 15 g 2,3,4,5-tetrahydro-1H-1-benzazepin-2-one (L. H. Briggs, *J. Chem. Soc.*, 937, 456) in 200 ml chloroform at 0° was added portionwise over 1 hour, 19 g phosphorus pentachloride followed by 140 mg iodine and the slow dropwise addition of 90 ml of 1M bromine in chloroform. The reaction was then warmed to room temperature and stirred for 1 hour. After concentration, the residue was poured onto ice and extracted with chloroform. The extracts were dried (MgSO$_4$) and concentrated in vacuo. The residue was purified by chromatography (silica, 2 ether: 1 hexane) to afford 3-bromo-2,3,4,5-tetrahydro-1H-1-benzaepin-2-one.

NMR (CDCl$_3$: δ2.4-3.0 (m, 4H); 4.4-4.7 (t, 1H); 7.2 (s, 4H); 9.2 (br.s, 1H).

To a solution of 9.98 g of the above bromide in 200 ml dimethylformamide was added 10.8 g sodium azide. After 12 hours at 60°, the solvent was removed in vacuo and the residue partitioned between chloroform and water. The organic extracts were dried (MgSO$_4$) and concentrated. Chromatography of the residue afforded pure 3-azido-2,3,4,5-tetrahydro-1H-1-benzazepin-2-one (m.p. 150-151° C.).

This azide was converted to 1-t-butoxycarbonylmethyl-3-azido-2,3,4,5-tetrahydro-1H-1-benzazepin-2-one following the procedure in Example 1, Step B (m.p. 103-104° C.).

The above azido ester was reduced in ethanol over 10% palladium on carbon to afford 1-t-butoxycarbonylmethyl-3-amino-2,3,4,5-tetrahydro-1H-1-benzazepin-2-one (m.p. 107-109° C.).

This amine was alkylated with methyl iodide via the benzalimine derivative as described in Example 3 to afford, after hydrolysis, 1-t-butoxycarbonylmethyl-3-amino-3-methyl-2,3,4,5-tetrahydro-1H-1-benzazepin-2-one.

This alkylated amine was converted to the title compound following the procedure in Example 1, Steps C-F.

NMR (D$_2$O, H$_2$O=4.8): δ1.1 (s, 3H); 1.4-3.2 (m, 8H); 4.3 (brs, 2H); 7.1 (brs, 9H).

EXAMPLE 7

1-Carbomethoxy-3-(1-carboethoxy-3-phenylpropyl)amino-7-phenylperhydroazepin-2-one Step A: 3-Bromo-7-phenylperhydroazepin-2-one To a solution of 25 g phosphorus pentachloride in 220 ml CH$_2$Cl$_2$ kept at 0° there was added a solution of 22 g 7-phenylcaprolactam and 18.9 g pyridine in 220 ml CH$_2$Cl$_2$. Portionwise addition of 45.1 g phenyltrimethylammonium tribromide was followed by allowing the reaction mixture to reach room temperature. After 3 hours, the reaction mixture was poured into ice water and extracted with CH$_2$Cl$_2$. The organic phase was washed with 5% aqueous sodium bisulfite. After drying and concentration, the crude residue was purified by chromatography over silica gel eluting with ethyl acetate:hexane (2:3). Concentration of the appropriate fractions afforded 16.3 g. 3-bromo-7-phenylperhydroazepin-2-one as a mixture of diastereomers.

Step B:
3-Bromo-1-t-butoxycarbonylmethyl-7-phenylperhydroazepin-2-one

A solution of 15.5 g of the lactam from Step A and 14.7 t-butyl iodoacetate in 150 ml tetrahydrofuran was added dropwise to a slurry of 1.45 g sodium hydride in 20 ml tetrahydrofuran. After 3 hr at room temperature the reaction was quenched by the addition of 15 ml sat. $NH_4Cl$ solution. The mixture was filtered and concentrated and the residue partitioned between $CHCl_3$ and $H_2O$. The crude product was obtained after drying and concentrating the $CHCl_3$ solution. Chromatography over silica gel with hexane: ethyl acetate (4:1) afforded two isomers of 3-bromo-1-t-butoxycarbonylmethyl-7-phenylperhydroazepin-2-one: isomer A (minor, elutes first), and isomer B (major, elutes second).

Step C:
3-Azido-1-t-butoxycarbonylmethyl-7-phenylperhydroazepin-2-one

A solution of 20 g of isomer B from Step B and 7.69 g lithium azide in 100 ml dimethylformamide was heated at 80° overnight. After concentration, the residue was partitioned between water and ethyl acetate. The organic phase was dried and concentrated to afford 3-azido-1-t-butoxycarbonylmethyl-7-phenylperhydroazepin-2-one which may be recrystallized from ethyl acetate-hexane.

NMR ($CDCl_3$, TMS): $\delta 1.45$ (s, 9H); $\delta 1.6$–2.7 (m, 6H); $\delta 3.3$ (d, 1H, J=17 hz); $\delta 4.0$ (d, 1H, J=17 hz); $\delta 4.4$ (broad m, 1H); $\delta 4.8$ (broad d, 1H); $\delta 7.25$ (s, 5H).

Step D:
3-Amino-1-t-butoxycarbonylmethyl-7-phenylperhydroazepin-2-one

A solution of 8.95 g of the azide from Step C in 75 ml ethanol was hydrogenated over 2 g 10% Pd-C at 45° C. for 5 hr. The solution was then filtered and concentrated to afford 8.3 g 3-amino-1-t-butoxycarbonylmethyl-7-phenylperhydroazepin-2-one.

NMR ($CDCl_3$, TMS): $\delta 1.4$ (s, 9H); $\delta 1.72.5$ (m+s, 8H); $\delta 3.4$ (d, 1H, J=17 hz); $\delta 3.95$ (d, 1H, J=17 hz); $\delta 4.0$ (broad m, 1H); $\delta 4.95$ (broad d, 1H); $\delta 7.3$ (s, 5H).

Step E:
1-t-Butoxycarbonylmethyl-3-(1-ethoxycarbonyl-3-phenylpropyl)amino-7-phenylperhydroazepin2-one A solution of 3.8 g of the amine from Step D, 3.7 g ethyl 2-oxo-4-phenylbutyrate, and 0.68 ml acetic acid in 50 ml ethanol was hydrogenated and the isomers separated by chromatography on silica gel using 1:1 ethylacetate:hexane to afford 1-t-butoxycarbonylmethyl-3-(1-ethoxycarbonyl-3-phenylpropyl)amino-7-phenylperhydroazepin-2-one:
Isomer A (elutes first) and isomer B (elutes second).

Step F:
1-Carboxymethyl-(1-ethoxycarbonyl-3-phenylpropyl)amino-7-phenylperhydroazepin-2-one Each of the isomers from Step E was treated with trifluoroacetic acid to afford the respective isomers of 1-carboxymethyl-3-(1-ethoxycarbonyl-3-phenylpropyl)amino-7-phenyperhydroazepin-2-one as the trifluoroacetate salt.

Isomer A: NMR ($CDCl_3$, TMS): $\delta 1.3$ (t); $\delta 1.5$–2.6 (m); $\delta 2.6$–3.1 (m); $\delta 3.6$–3.9 (m); $\delta 4.2$ (q); $\delta 4.0$–4.8 (m); $\delta 7.2$ (s); $\delta 8.9$ (broad s).

Isomer B: NMR (DMSO-$d_6$, TMS): $\delta 1.27$ (t); $\delta 1.6$–3.1 (m); $\delta 3.7$–4.5 (m+q); $\delta 4.7$ (broad); 67 5.1 (broad): $\delta 7.2$ (s); $\delta 7.3$ (s).

Step G:
1-Carbomethoxymethyl-3-(1-carbethoxy-3-phenylpropyl)amino-7-phenylperhydroazepin-2-one (isomer B)

To a solution of 0.1 gm of 1-carboxymethyl-3-(1-ethoxycarbonyl-3-phenylpropyl)amino-7-phenylperhydroazepin-2-one (Isomer B, Step F) in 10 mL methylene chloride was added a solution of diazomethane in ether until TLC (silica, 7:3, ethylacetate:hexane) indicated reaction was complete. The reaction mixture was then concentrated at reduced pressure and purified by chromatography (silica, 7:3 ethylacetate:hexane) to give 60 mg of diester.

TLC (silica, 7:3, ethylacetate:hexane) $R_f=0.44$

NMR ($CDCl_3$, TMS) 1.3 (t, 3H); 1.6–2.4 (m, 8H); 2.6–3.0 (m, 3H); 3.55 (s, 3H); 3.2–4.0 (m, 9H); 4.175 (9, 2H); 7.2 (s, 5H), 7.3 (s, 5H); mass spectrum FAB m/e 467 ($M^+ +1$).

EXAMPLE 8

1-Carbomethoxymethyl-3-(1-carbomethoxy-3-phenylpropyl)amino-3-methyl homodihydrocarbostyril A solution of 0.06 gm of 1-carboxymethyl-3-(1-carboxy-3-phenylpropyl)amino-3-methyl-2,3,4,5-tetrahydro-1H-1-benzazepin-2-one (Example 6) in 10 ml of methanol was saturated with HCl gas at 0° C. The reaction was sealed and stirred at room temperature for 12 hours whereupon it was concentrated at reduced pressure. The reaction mixture was then partitioned between ethylacetate and a saturated solution of $NaHCO_3$ in $H_2O$. The aqueous layer was extracted twice with ethylacetate and the combined organic fractions were filtered through $MgSO_4$, concentrated in vacuo, and chromatographed (silica, 1:1 ethylacetate:hexane) to give 0.045 gm of the title compound.

TLC (silica, 1:1, ethylacetate:hexane) $R_f=0.60$

NMR ($CDCl_3$, TMS) 1.1 (s, 3H); 2.5–3.4 (m, 10H); 3.65 (s, 3H); 3.7 (s, 3H); 3.55 (s, 2H); 7.1 (bs, 9H).

Anal. ($C_{25}H_{30}N_2O_5$). Calc.: H, 6.90; C, 68.48; N, 6.39. Found: H, 6.91; C, 68.71; N, 6.28.

What is claimed:

1. A method of antagonizing the binding of cholecystokinins to cholecystokinin receptors in a mammal having a gastrointestinal disorder which comprises administering to said mammal an effective amount of a compound having the formula:

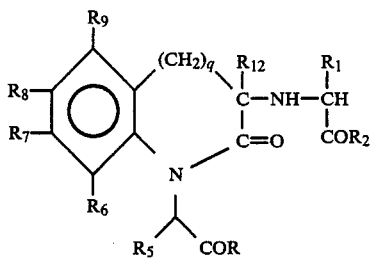

wherein:

R and $R_2$ are independently hydroxyl, loweralkoxy, aryloxy, aralkoxy, and $NR^{10}R^{11}$ wherein $R^{10}$ and $R^{11}$ are independently hydrogen, loweralkyl, loweralkenyl, acyloxyloweralkyl, aryl, aralkyl, carboxyloweralkyl, carboxamido loweralkyl, substituted loweralkyl wherein the substituents are monohydroxy, dihydroxy, or acylamino;

$R_1$ is hydrogen;

alkyl of from 1 to 12 carbon atoms which include branched, cyclic and unsaturated alkyl groups;

substituted loweralkyl wherein the substituent can be halo, hydroxy, carboxy, carboxamido, loweralkylthio, loweralkoxy, loweralkoxycarbonyl, loweraralkoxycarbonyl, amino, loweralkylamino, lowerdialkylamino, acylamino, substituted loweralkylamino wherein the substituent can be halo, hydroxy, alkoxy or cyano; arloweralkylamino; cyclic amino; oxo, thio or ureido; aryloxy; arylthio; aralkyloxy; aralkylthio; benzofused cycloalkyl or bicycloalkyl of from 8-12 carbon atoms;

aryl or heteroaryl which may be mono-, di- or trisubstituted by loweralkyl, hydroxy, loweralkoxy, halo, amino, acylamino, loweralkylthio or aminoloweralkyl;

benzofused cycloalkyl or bicycloalkyl of from 8 to 12 carbon atoms;

arloweralkyl; arloweralkenyl; heteroloweralkyl and heteroloweralkenyl in which the aryl or heteroaryl rings may be mono-, di- or tri-substituted by halo, loweralkyl, hydroxy, loweralkoxy, amino, loweralkylamino, diloweralkylamino, aminoloweralkyl, acylamino, carboxy, haloloweralkyl, nitro, cyano or sulfonamido;

aralkyl or heteroaralkyl which include branched loweralkyl groups;

substituted aralkyl or substituted heteroaralkyl which include branched loweralkyl groups wherein the loweralkyl groups can be substituted by amino, acylamino, or hydroxyl and the aryl and heteroaryl groups can be substituted by halo, dihalo, loweralkyl, hydroxy, loweralkoxy, arloxy, arolyl, arylthio, amino, aminoloweralkyl, loweralkanoylamino, aroylamino, lowerdialkylamino, loweralkylamino, hydroxy, hydroxyloweralkyl, trihaloloweralkyl, nitro, cyano, or sulfonamido;

any of the arloweralkyl or alkenyl and heteroloweralkyl or alkenyl groups described above in which the aryl or heteroaryl ring is partially or completely hydrogenated;

substituted loweralkyl having the formula $R_A{}^1(CH_2)_n$—Q—$(CH_2)_m$ wherein n is 0–2, m is 1–3, $R_A{}^1$ is aryl or heteroaryl optionally substituted by amino, lowerdialkylamino, loweralkylamino, hydroxy, hydroxyloweralkyl, aminoloweralkyl, trihaloloweralkyl, cyano, nitro, sulfonamido, aroyl, loweralkyl, halo, dihalo, and loweralkoxy, and Q is O, S, SO, $SO_2$, N—$R_B{}^1$, $CONR_C{}^1$, $NR_C{}^1CO$, CH=CH wherein $R_B{}^1$ is hydrogen, loweralkyl, aryl, aralkyl, loweralkanoyl, or aroyl, and $R_C{}^1$ is hydrogen, or loweralkyl;

$R_3$ is hydrogen, or loweralkyl;

$R_4$ is hydrogen, loweralkyl, aryl, or substituted aryl wherein the substituent is halo, alkyl, or alkoxy;

$R_5$ is hydrogen, loweralkyl, or aryl;

$R_6$ $R_7$, $R_8$ and $R_9$ can be the same or different or each can independently be hydrogen, loweralkyl, loweralkoxy, or halo;

$R_{12}$ is loweralkyl;

n is 1–4;

q is 2; or pharmaceutically acceptable salts thereof.

2. The method of claim 1 wherein said compound is: 1-carbomethoxymethyl-3-(1-carbethoxy-3-phenylpropyl)amino-7-phenylperhydroazepin-2-one.

* * * * *